(12) United States Patent
Baraka et al.

(10) Patent No.: US 10,722,406 B1
(45) Date of Patent: Jul. 28, 2020

(54) MALE URINARY INCONTINENCE PROTECTOR

(71) Applicant: Sasori Corporation, Boston, MA (US)

(72) Inventors: Analesa Rosemary Baraka, Boston, MA (US); Richard James Walter Mansfield, Cambridge, MA (US)

(73) Assignee: Sasori Corporation, Boston, MA (US)

( * ) Notice: Subject to any disclaimer, the term of this patent is extended or adjusted under 35 U.S.C. 154(b) by 0 days.

(21) Appl. No.: 15/394,772

(22) Filed: Dec. 29, 2016

Related U.S. Application Data

(60) Provisional application No. 62/272,615, filed on Dec. 29, 2015.

(51) Int. Cl.
| | |
|---|---|
| *A61F 5/44* | (2006.01) |
| *A61F 13/471* | (2006.01) |
| *A61F 13/42* | (2006.01) |
| *A61F 13/58* | (2006.01) |
| *A61F 13/539* | (2006.01) |
| *A61F 13/15* | (2006.01) |
| *A61F 13/53* | (2006.01) |

(52) U.S. Cl.
CPC ............ *A61F 13/471* (2013.01); *A61F 13/42* (2013.01); *A61F 13/539* (2013.01); *A61F 13/58* (2013.01); *A61F 2013/15121* (2013.01); *A61F 2013/15487* (2013.01); *A61F 2013/422* (2013.01); *A61F 2013/530481* (2013.01); *A61F 2013/582* (2013.01)

(58) Field of Classification Search
CPC ...... A61F 13/471; A61F 13/42; A61F 13/539; A61F 13/58; A61F 2013/15121; A61F 2013/15487; A61F 2013/422; A61F 2013/530481; A61F 2013/582

USPC ......................................................... 604/349
See application file for complete search history.

(56) References Cited

U.S. PATENT DOCUMENTS

| | | | | |
|---|---|---|---|---|
| 3,884,072 | A | * 5/1975 | Cheng ................... | A61B 5/208 73/215 |
| 4,590,931 | A | * 5/1986 | Kidwell, Jr. ............ | A61F 5/40 128/DIG. 15 |
| 5,695,485 | A | * 12/1997 | Duperret ................ | A61F 13/471 604/349 |
| 2002/0070864 | A1 | * 6/2002 | Jeutter ................... | A61F 13/42 340/573.1 |
| 2003/0166293 | A1 | * 9/2003 | Kritzman ........... | A61B 5/14539 436/111 |
| 2004/0106909 | A1 | * 6/2004 | Browning ............... | A61F 5/453 604/349 |
| 2006/0149196 | A1 | * 7/2006 | Bjornberg ............... | A61F 5/453 604/349 |
| 2006/0229576 | A1 | * 10/2006 | Conway .................. | A61F 5/453 604/349 |
| 2009/0130195 | A1 | * 5/2009 | Acevedo-Duncan ...... | A61K 9/127 424/450 |
| 2010/0160882 | A1 | * 6/2010 | Lowe ..................... | A61F 13/42 604/361 |
| 2013/0019374 | A1 | * 1/2013 | Schwartz ................ | A61F 5/00 2/69 |

\* cited by examiner

*Primary Examiner* — Andrew J Mensh
(74) *Attorney, Agent, or Firm* — William Mansfield

(57) ABSTRACT

Among other things a male urinary protective device for mild and moderate stress and urge incontinence providing extended protection, discreet appearance for active users, single-step reusable adjustment while maintaining skin integrity.

9 Claims, 7 Drawing Sheets

| Condition | Indicator | Disease/Diagnosis |
|---|---|---|
| Protein | Tetrabromophenol Blue + Protein = Yellow | Renal Damage (proteinuria) |
| Blood (Hemoglobin) | Tetramethylbenzidine + hemoglobin = Green to Dark Blue | Kidney Disease (Kidney stones, glomerular disease, tumor) |
| Glucose | Glucose + Glucose Oxidase + Peroxidase Chromogen = Color | Diabetes Mellitus |
| Ketone | Sodium Nitroferricyanide + Acetoacetic Acid + Alkali = Pink-Magenta | Metabolic Imbalance (e.g., Diabetes Type I) |
| Bilirubin | Bilirubin Glucuronide + Diazonium Salt = Azo Dye (Violet) | Liver Disease (Jaundice, Cirrhosis) |
| Leukocytes | Leukocyte Esterase + Indocarboxylic Acid Ester + Diazonium Salt = Azo Dye (Violet) | Bacterial Urinary Infection |
| Prostate Specific Antigen | Immunoassay | Prostatitis, Hyperplagia, Prostate Tumor |

FIG. 7

MALE URINARY INCONTINENCE PROTECTOR

TECHNICAL FIELD

The present invention relates generally to a urine absorbent pouch for male incontinence.

BACKGROUND

Involuntary release of urine is a problem, particularly for aging men, when the sphincter muscles, at the base of the urethra as it exits the bladder, weaken as the result of disease progression, such as diabetes, or following a surgical procedure, such as transurethral bladder resection or radical prostatectomy. Complete lack of bladder control led to the invention of the Foley catheter, which is often used on a temporary basis when bladder control can be regained so that only minor intermittent leakage remains. However, weakening of control of the sphincter surrounding the urethra subjects the patient to, for example, stress incontinence from increased abdominal pressure resulting from a simple cough, or sneeze. Such leakage not only creates psychological distress but can also lead to skin or urinary tract infections. An increasing number of aging but active and mobile men, amounting to several million in the United States alone, have to deal with this problem and require an easy to use, economical and discreet solution, thereby creating a demand for a urinary incontinence device to handle mild to moderate incontinence.

A variety of approaches have attempted to meet these needs. Incontinence small pads, which make for additional protection and for better fit, being worn in an incontinence garment, are often used. Many incontinence products are modifications of existing products not suited for men or for a man's self-image, e.g., Depend® (Depend® is registered trademark of Kimberly-Clark, Inc. of Irving, Tex.) diapers or a male incontinence shield adapted from the female sanitary garment, which requires a man to apply a pad with an adhesive layer to their undergarment. While these pads may in many cases provide sufficient storage capacity, they seem more appropriate for the female anatomy than for the male anatomy. Either such a pad is pressed so tightly against the body, e.g., by an incontinence garment, such that wearing comfort is affected, or there is a risk of leakage. In particular, since the penis and thereby the urinary duct has some freedom to move, urine may be deposited towards the edge or even outside the pad. Male shields currently mirror female protective garments and do not take into account that the scrotum and testes are also in contact with this garment so such shields can contribute to, and have contributed to, impaired skin integrity, moreover, they are bulky and non-discreet. Depend® undergarments contribute to the psychological undermining and further emasculating of the man recovering from a temporary/permanent medical issue. Moreover, persons who have worn boxer undergarments all their adult life are now forced to change their lifestyle and purchase undergarments that they have never worn.

On the other hand, a condom catheter has a tendency to dislodge and an incontinence pouch constructed using a modified Cunningham hard plastic clip can only be used for 15 minutes at a time to avoid blood circulation blockage.

A number of devices have been proposed for urinary incontinence where some bladder control is retained. One proposed solution ("Urine absorbent pouch for male incontinence", Lucas Bak Bindal, U.S. Patent Application Serial Number 2011/0015604A1, filed July/2007) is inconvenient as it requires the user to insert his penis through the moldable hole on one side of the flap, which adheres to the other side, then he must assemble the device in such a way that it stays in place, which assumes the penis does not retract. A second proposed solution (Lars Mattsson, "Male Incontinence Pouch", U.S. Pat. No. 6,209,142, Issued April/2001), which can accommodate only the penis or the penis plus scrotum, has the possibility of leakage if the complicated seals on the upper section are not secured. A third proposed solution (John A. Rooyakkers, "Absorbent Genitalia Pouch for Incontinent Males, U.S. Pat. No. 4,772,280, Issued September/1988) is designed to accommodate both penis and scrotum; however, such an approach has the disadvantage of skin breakdown due to accumulating moisture thus creating a high potential for skin and scrotum sheer. Moreover, users mustwear tight undergarments or additional garments to keep the device in place but it could still move and not offer the anticipated level of urinary incontinence protection. A fourth approach (Edward E. Elson et. al., "Male Urinary Incontinence Sheath Having Gel Adhesive and Elastic Securement Tape", U.S. Pat. No. 7,166,092, Granted Janurary/2007) is designed for heavy urinary incontinence with a connection adaptor able to attach to a leg bag (second urinary storage device) secured to the user's leg. The adhesive attached to the user's skin impairs the skin integrity with the resulting risk for infection. There is also a risk for urine backup from the air lock in the drain tube or from a dysfunctional coupler; moreover, there is a plastic device, which traps body heat thereby risking impaired skin integrity. A fifth approach (Achim Schmitt et. al, "Male Incontinence Device", European Patent Office Patent Application Serial No. EP 1136051, filed March/2000) is designed to accommodate the entire male genitalia both scrotum and penis thereby exposing the scrotum to urine, which risks skin breaks and resulting infections. It is designed with three layers of protection, which may not be needed with the present availability of super absorbent material.

In general, there is an unmet need for a practical and efficient incontinence protection device designed for the male anatomy with a comfortable, secure fit designed for 24-hour protection; discreet outer appearance; a moisture lock barrier to protect against skin breakdown; and protection from scrotum sheer. The need is particularly great for men having undergone a prostatectomy for cancer or men with lower urinary tract symptoms, such as urgency and pre- and post-void urinary dribble, who are unable to make it to the bathroom in time.

SUMMARY

The main purpose of the present invention is to eliminate the known drawbacks that impair existing incontinence pouches by providing an incontinence pouch with the following features:

(a) Contoured to the phallus and meatus to maintain skin integrity thus avoiding skin abrasion with scrotum sheer;
(b) Providing discreet protection against socially embarrassing incontinence from light to moderate drips and dribbles by means of a small, light-weight incontinence protector rather than a diaper so as to minimize psychological stress;
(c) Compatible with men's apparel such as boxers and close-fitting trousers and jeans; (d) Slim design so spare devices can be carried discreetly;
(e) Reliably wicks away urine when used by an active wearer without giving a wet or clammy feeling when in use;
(f) Provides protection from odors;
(g) Easily positioned and applied;

(h) Readily and economically produced.

These and other objectives are addressed by the present invention as will be apparent from the following description.

In general, in an aspect, a male incontinence protection device, which is cylindrically structured to cover the phallus and urinary meatus, providing single-step adjustment and trapping incontinence in a moisture-lock garment.

Implementations may include one or a combination of any two or more of the following features. The capped cylinder contoured to cover only the phallus and meatus comprising an inner liquid-permeable layer, an outer liquid-impermeable layer, a middle layer of superabsorbent material to retain urine odorlessly. The base of the cylinder has one or more elasticized threads together with a single-step adjustable fastener that is releasable. The top portion of the middle layer serves as a color guard by alerting the user with a marked color change when the urinary pouch is moist and needs to be replaced. In some embodiments, embedded in the top of the inner layer, near the meatus, is a biosensor that can detect components of the urine pertinent to health conditions and provides a measure of the volume of urine excreted.

In general, in another aspect, a simple, efficient method for rendering the male incontinence device from components in a series of steps.

Implementations may include one or a combination of any two or more of the following steps. A step for forming the inner liquid-permeable layer on a tempered glass rod contoured to the male phallus and meatus. A step for adding superabsorbent material to cover the inner layer. A step for adding a color guard layer at the top of the cylinder covered by superabsorbent material. A step for moisture sealing the device with a liquid-impermeable layer over the superabsorbent layer. A step for affixing to the base of the cylinder one or more elasticized threads together with an adjustable, reusable fastener to secure the incontinence protective device on the user.

These and other aspects, features, implementations, and advantages, and combinations of them, can be expressed as methods, apparatus, systems, components, program products, business methods, and means or steps for performing functions, or combinations of them.

Other features, aspects, implementations, and advantages will become apparent from the description, the drawings, and the claims.

BRIEF DESCRIPTION OF THE DRAWINGS

The accompanying drawings illustrate several embodiments of the invention and, together with the description, serve to explain the principles of the invention according to the embodiments. One skilled in the art will recognize the particular embodiments illustrated in the drawings are merely exemplary, and are not intended to limit the scope of the present invention.

FIG. 68 illustrates an exemplary method of forming a male urinary incontinence protective device according to the present invention.

FIG. 7 illustrates an exemplary set of diagnostic tests embodied in the biosensory system.

DETAILED DESCRIPTION OF THE EMBODIMENTS

Figure 1:
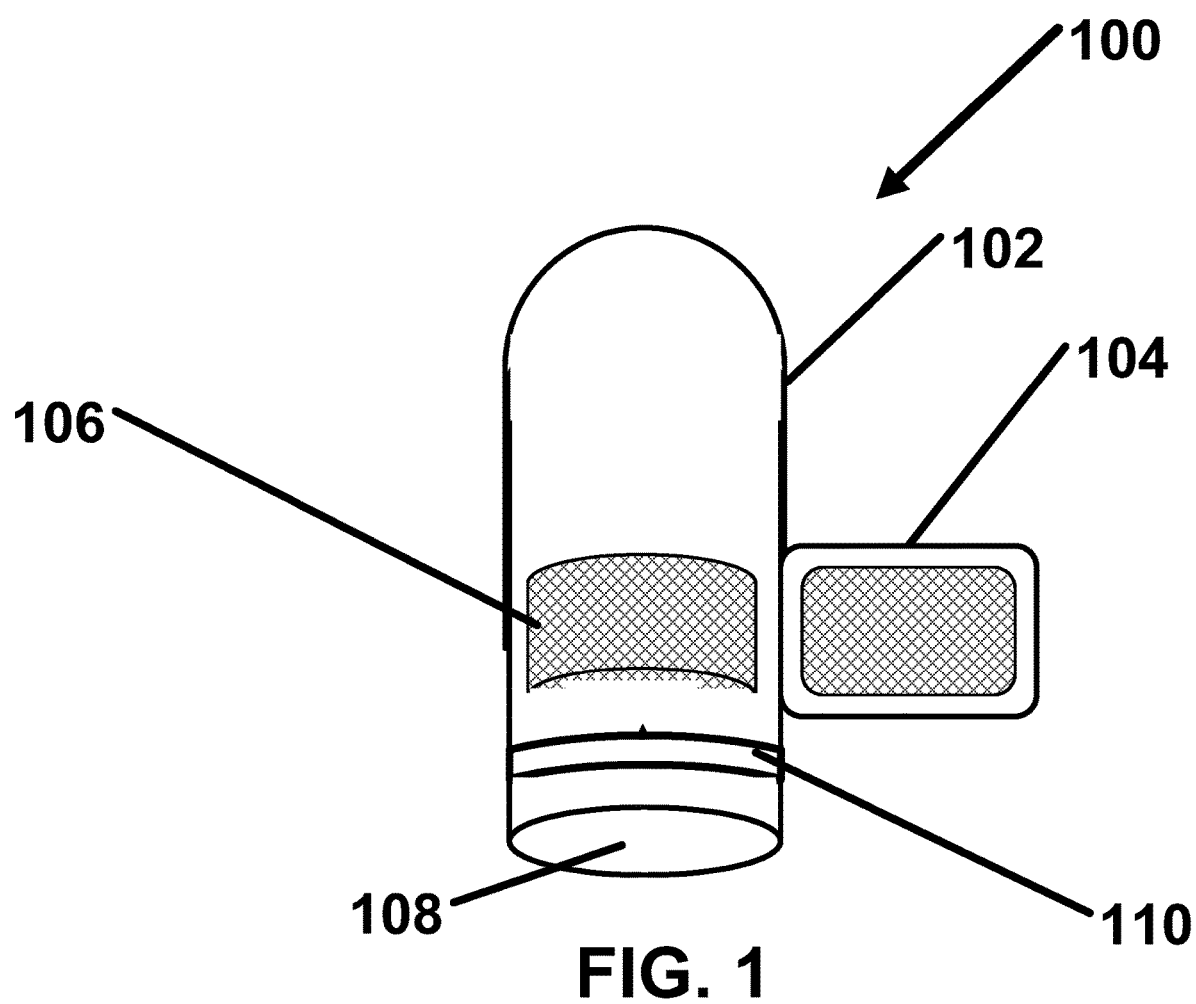
FIG. 1 is a Side Perspective View of an exemplary male urinary incontinence protector device according to the present invention.

Various techniques will now be described in detail with reference to a few example embodiments thereof as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well known process steps and/or structures have not been described in detail in order not to obscure some of the aspects and/or features described or referenced herein.

One or more different inventions may be described in the instant patent application. Further, for one or more of the invention(s) described herein, numerous embodiments may be described in the instant patent application, and are presented for illustrative purposes only. The described embodiments are not intended to be limiting in any sense. One or more of the invention(s) may be widely applicable to numerous embodiments, as is readily apparent from the disclosure. These embodiments are described in sufficient detail to enable those skilled in the art to practice one or more of the invention(s), and it is to be understood that the other embodiments may be utilized and that structural, logical, software, electrical, mechanical, and other changes may be made without departing from the scope of the one or more invention(s). Accordingly, those skilled in the art will recognize that the one or more of the invention(s) may be practiced in various modifications and alterations. Particular features in the one or more invention(s) may be described with reference to one or more particular embodiments of figures that form a part of the present disclosure, and in which are shown, by way of illustration, specific embodiments of the one or more invention(s). It should be understood, however, that such features are not limited to usage in the one or more particular embodiments or to figures with reference to which they are described. The present disclosure is neither a literal description of all embodiments of one or more of the invention(s) nor a listing of features of one or more of the invention(s) that must be present in all embodiments.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. To the contrary, a variety of optional components are described to illustrate the wide variety of possible embodiments of the invention.

Further, although process steps, method steps, algorithms or the like may be described in a sequential order, such processes, methods and algorithms may be configured to work in alternate orders. In other words, any sequence or order of steps that may be described in the instant patent application does not, in and of itself, indicate a requirement that the steps be performed in that order. The steps of described processes may be performed in any practical order. Further, some steps maybe performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

When a single device or article is described, more than one device/article (whether or not they cooperate) may be used in place of a single device/article. Similarly, where more than one device or article is described (whether or not they cooperate), a single device/article may be used in place of the more than one device or article.

Techniques and mechanisms described or referenced herein will sometimes be described in singular form for clarity. However, particular embodiments include multiple iterations of a technique or multiple instantiations of a mechanism unless noted otherwise.

The system described here enables a male with minor urinary incontinence to proceed with normal activities without distress or risk of skin or urinary tract infection from unabsorbed urine fluid.

As desired, a urinary incontinence protector may include more or fewer than the components illustrated. The urinary incontinence device is described above with reference to diagrams of systems, methods, and apparatuses according to examples. Generally, the urinary incontinence device disclosed herein may be implemented by an efficient manufacturing process.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

As shown in FIG. 1 the urinary incontinence device, 100, comprises a cylindrical pouch, 102, with a smooth rounded apical cap and with an adjustable fastener, 104, at the base attaching to a portion on the circumference at the base, 106. The pouch, 102, is placed over the user's penis through the entryway, 108, then said pouch, 102, is secured in place with the adjustable fastener, 104, which is releasable. The said fastener, 104, has a cylinder-facing inner adhesive surface so that, after adjustment to accommodate the user's penis, the fastener tab engages a corresponding adhesive surface. The adhesive surfaces may be formed by any reusable adhering surface, including, but not limited to, a variety of sealing material such as glue, cold-glue, hotmelt, lacquer, wax, ZipLok® ribbons and Velcro® tab fasteners. Velcro® is a registered trademark of Velcro USA, having an office at 406 Brown Avenue, Manchester, N.H. 03103. ZipLok® is a registered trademark of S.C. Johnson & Son, having an office at 1525 Howe Street, Racine, Wis., 53403. The base of the pouch, 102, is threaded along its circumference with one or more bands of elastic thread shirring, 110, such as Gutermann® Thread Elastic, Oritz® Elastic Sewing Thread, Singer® Elastic Sewing Thread, or Maxi-Lock® Stretch Thread for gathering, crimping and smocking. Gutermann® is a registered trademark of GOtermann of America, Inc., having an office at 24 American Street, P.O. Box 507, Mount Holly, N.C. 28120; Oritz® is a registered trademark of Prym Consumer USA Inc., having an office in Spartanburg, S.C.; Singer® is a registered trademark of Singer Corporation, having an office at La Vergne, Tenn., USA; and Maxi-Lock® is a registered trademark of American & Efird Enterprises, Inc., having an office at 22 American Street, P.O. Box 507, Mt. Holly, N.C., 28120. The combination of the said fastener, 108, and the said elastic thread bands, 110, secures the pouch, 102, to the wearer without adversely affecting circulation.

Figure 2:
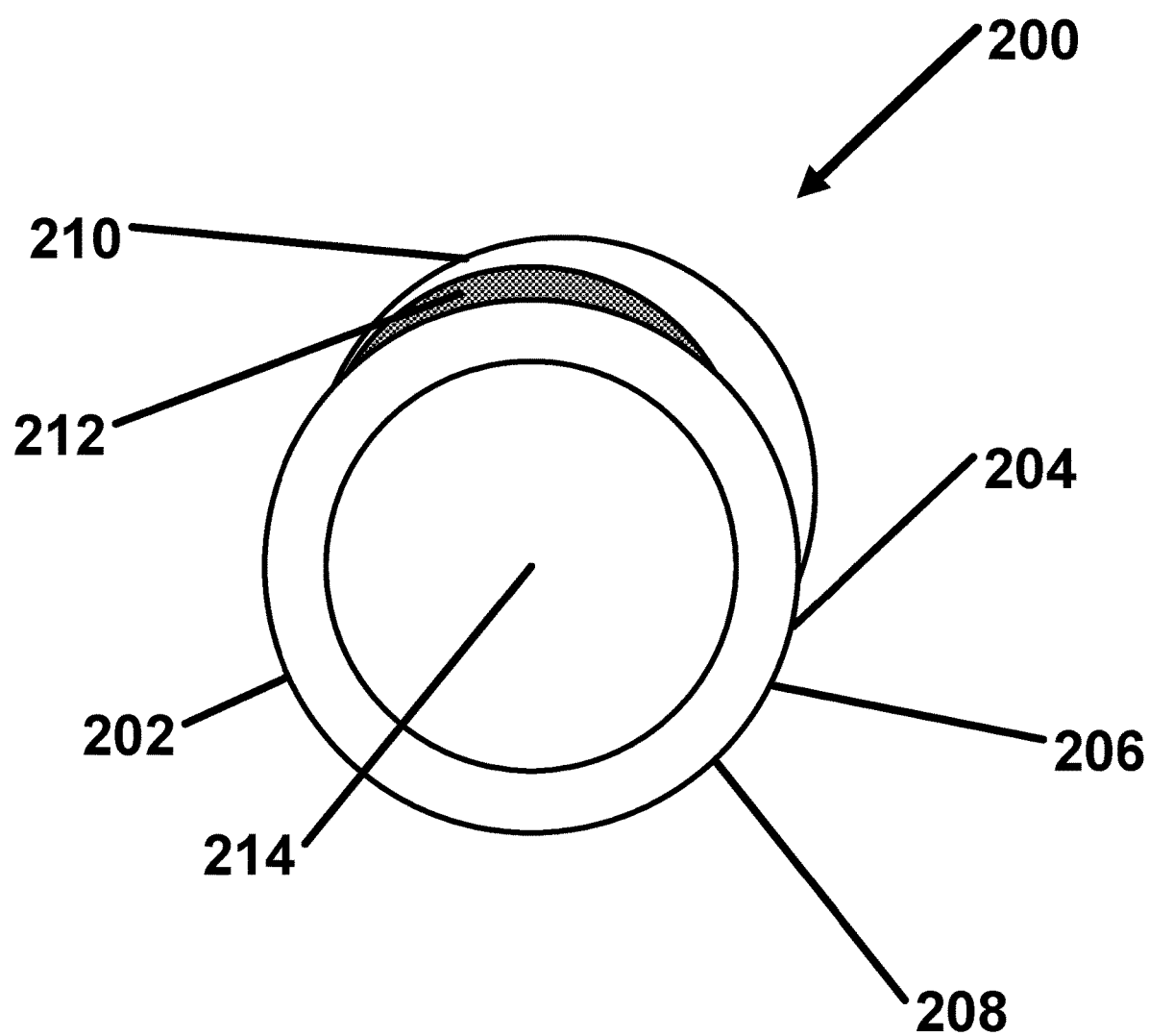
FIG. 2 is a Base End-on View of an exemplary male urinary incontinence protector device according to the present invention in fully fastened position.

In FIG. 2 the Base End-on View, 200, of an exemplary male urinary pouch shows the base end Entryway, 202, for the user's penis with the layer wall comprising an outer liquid-impermeable surface, 204, super absorbent filling, 206, and an inner liquid-permeable layer, 208. For optimal absorbance and less sag the liquid-permeable layer, 208, which could be carded cellulose or a perforated polymer sheet, is spun-bonded to the superabsorbent filling, 206. For the superabsorbent layer, polymers, such as starch-derived hydrogels and cross-linked acrylonitrile, may be used as they are capable of retaining large quantities of liquid by forming gel structures. Alternately, or in addition, an air-formed mixture of melt-blown polypropylene with wood fibers provides absorbance and structure. Preferred are the particulate superabsorbents, such as Grain Processing Corporation's Water-Lock® J-S00, or sodium polyacrylate, which is an integrally bonded layer structure. Water-Lock® is a registered trademark of Grain Processing Corporation, 1600 Oregon Street, Muscatine, Iowa 52761. The outer liquid-impermeable layer, 202, may be a heat-sealed outer liquid-proof polyethylene layer for greater integrity of the device.

The fastener, 210, is shown in closed position, for example, by use of a Velcro® adhesive patch pressure sealed against a corresponding Velcro® adhesive patch. The fastener tab itself, 210, is attached to the sheath using glue, adhesive, ultrasonic bonds, heat bonds, pressure bonds, heat and pressure bonds, or a combination of any of the aforementioned.

Figure 3:
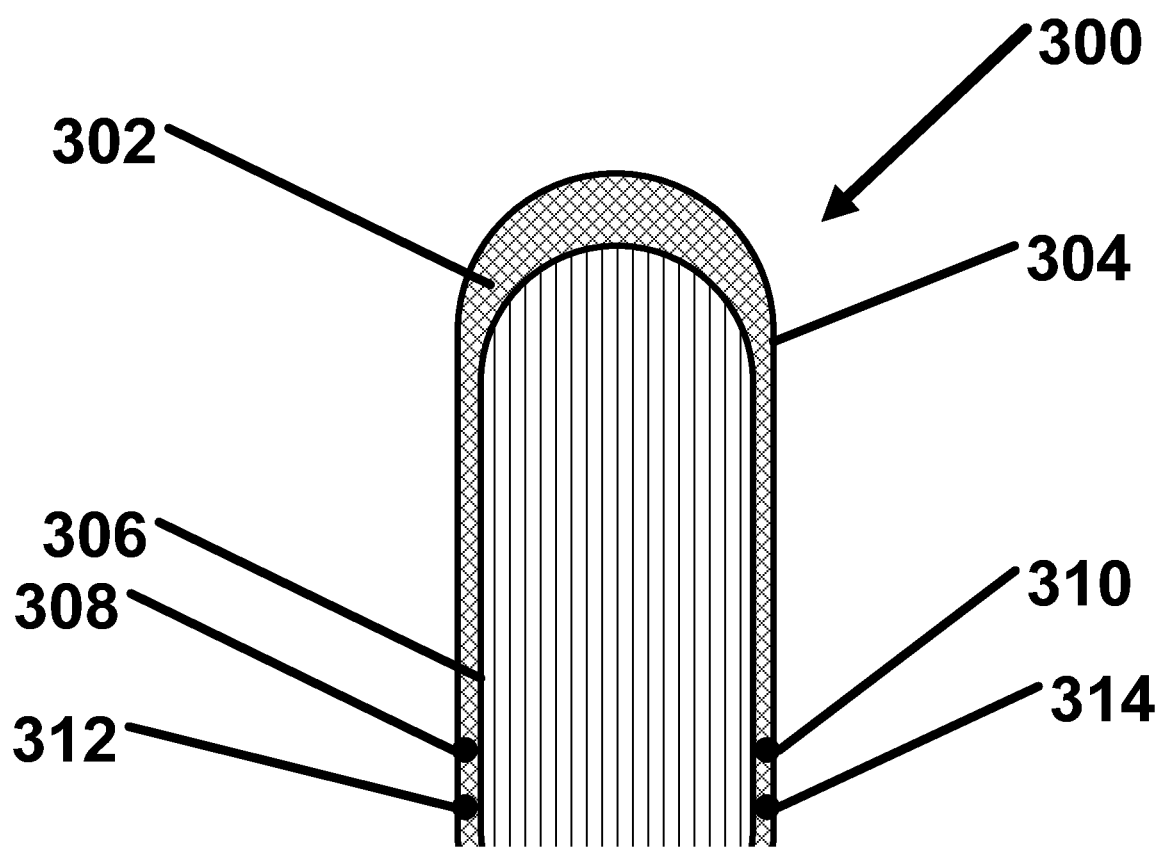
FIG. 3 shows a Midline Cross Section of an exemplary male urinary pouch.

As shown in FIG. 3, the Midline Cross Section, 300, of an exemplary urinary male urinary pouch comprises a layer of superabsorbent material, 302, between an outer liquid-impervious layer, 304, and an inner liquid-permeable layer, 306, with the layer of superabsorbent material thicker near the apex of the pouch. The end of the male urinary pouch is secured by encircling elasticized threads as indicated by 308, 310, 312, and 314.

Figure 4:
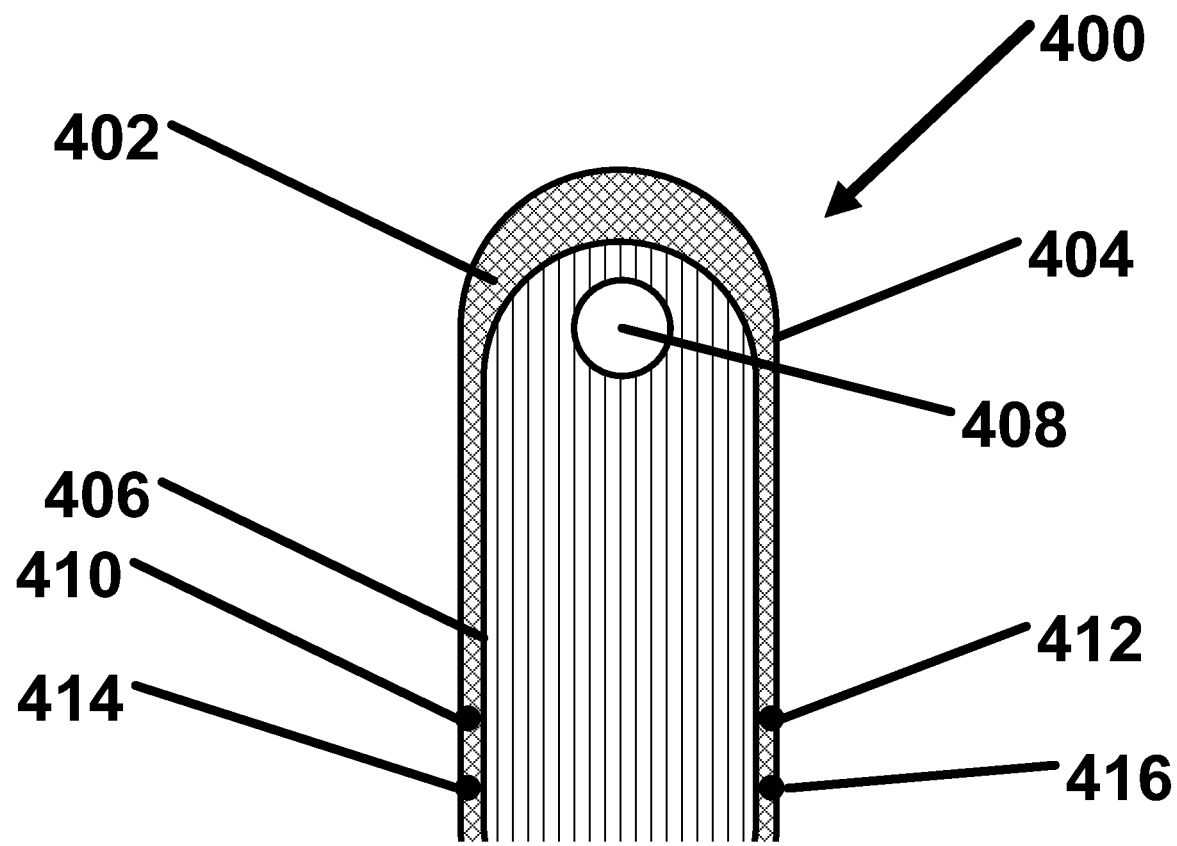
FIG. 4 shows a Midline Cross Section of an alternate embodiment of an exemplary male urinary pouch.

As shown in FIG. 4 the Midline Cross Section, 400, of an exemplary male urinary pouch comprises a layer of superabsorbent material, 402, between an outer liquid-impervious layer, 404, and an inner liquid-permeable layer, 406, with the layer of superabsorbent material thicker near the apex of the pouch. Near the apex also on the ventral side is an exemplary biosensor, 408. The base end of the male urinary pouch is secured by encircling elasticized threads as indicated by 410,412,414, and 416.

Figure 5:
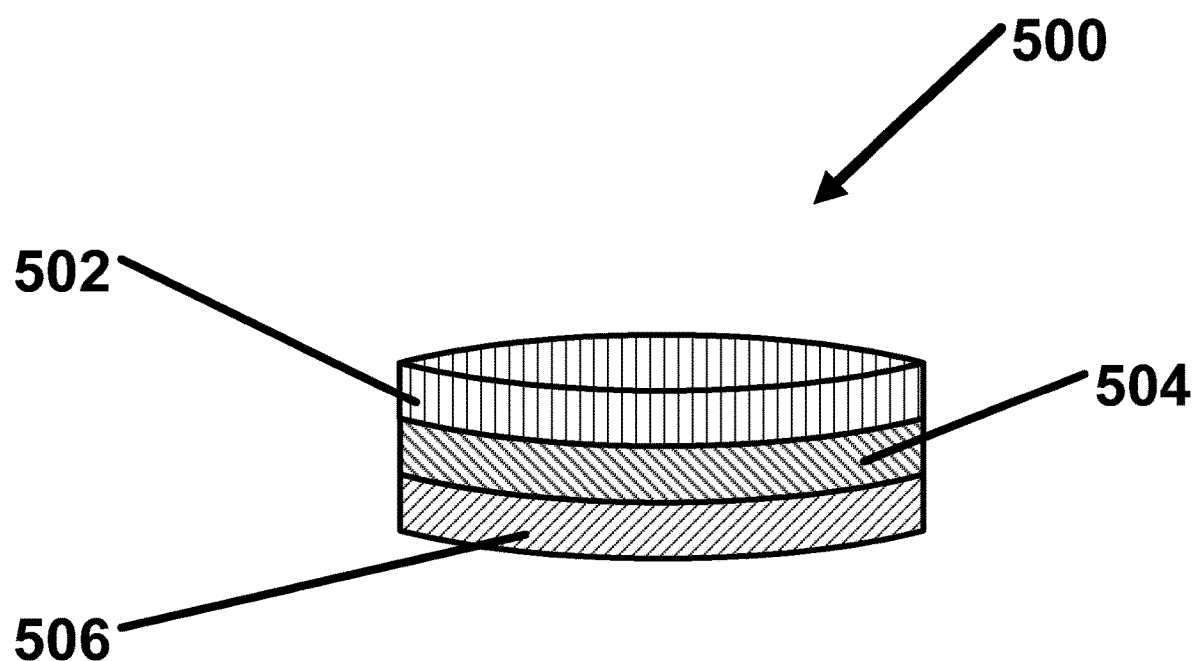
FIG. 5 shows an exemplary active RFID biosensor incorporated in an exemplary male incontinence device.

As shown in FIG. 5, an exemplary RFID biosensor system, 500, embedded in a depression of the wall of the male urinary incontinence device, comprises a multilayer sandwich with the biosensor, 502, uppermost below which is an active RFID unit, 504, powered by a thermal gradient battery, 506, facing the wall. The active RFID unit, 504, transmits biosensor data to the user's computerized sports watch, such as a FitBit® or an Apple iWatch®, that in turn can consolidate the data and send preliminary analyses to the Internet Cloud as part of diagnostic monitoring of the user. FitBit® is a registered trademark of Fitbit, Inc., having an office at 405 Howard Street, Suite 550, San Francisco, Calif. 94105 and iWatch® is a registered trademark of Apple, Inc., having an office at 1 Infinite Loop Cupertino, Calif. 95014. Moreover, the contents of the urine released may contain biomarkers that can be used diagnostically for a number of conditions to aid in restoring health and in prolonging quality of life.

Figure 6A:
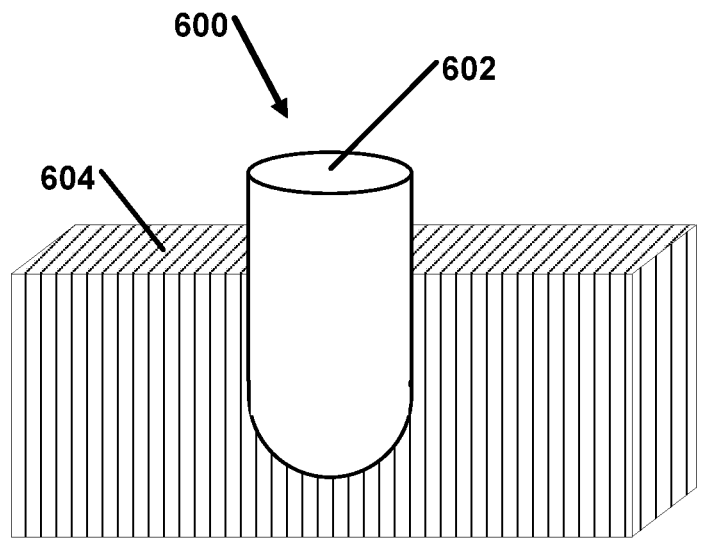
FIG. 6A illustrates an exemplary method of forming a male urinary incontinence protective device according to the present invention.

FIG. 6 illustrates an exemplary method of forming a male urinary incontinence protective device according to the present invention, 600. FIG. 6A shows a tempered glass rod, 602, lowered into a vat of molten plastic, 604, one or more times to form the liquid-permeable inner lining of the male urinary incontinence protective device. This manufacturing method is similar in some respects to that used for manufacturing condoms from rubber latex in which a tempered glass rod, termed a spandrel, is repeatedly dipped into a vat of molten latex and dried by circulating hot air between dips.

Figure 6B:
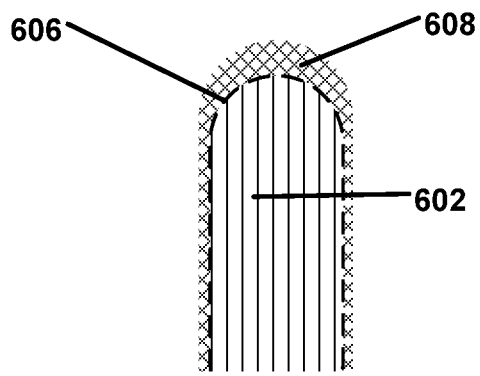
FIG. 6C illustrates an exemplary method of forming a male urinary incontinence protective device according to the present invention.

FIG. 6B shows a Midline Cross Section of said tempered glass, 602, with the finished liquid-permeable plastic layer, 606, onto which is sprayed a layer of superabsorbent material, 608, that adheres to the said inner layer, 606, via, for example, use of an alcohol-based adhesive that evaporates.

Figure 6C:
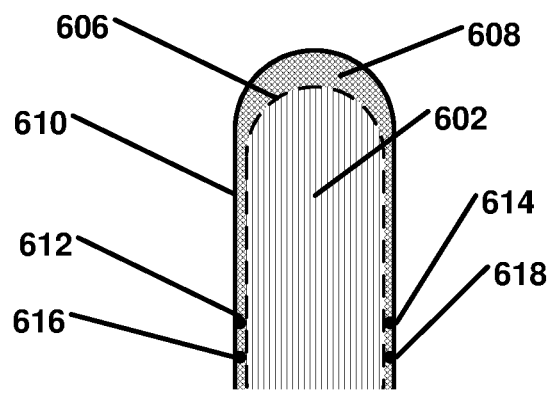

FIG. 6C shows a Midline Cross Section of said tempered glass, 602, showing the said inner liquid-permeable plastic layer, 606, the layer of said superabsorbent material, 608, onto which is positioned a liquid-impermeable layer, 610, which can be shrink-wrapped to seal the sheath from openings that would enable leaks. A preferred two-layer impermeable covering material is a coextruded material in which a polymer, generally polypropylene, is extruded onto a thin, spun-bonded fabric. Such a material has a cloth-like feeling against the skin, yet is strong and low in both cost and weight as a minimum amount of the polymer is utilized. Finally an operational means to adjust the base width, such as the fastener tab, 104, shown in FIG. 1 is attached, for example, by an adhesive, such as industrial glue. In addition, the end of the male urinary pouch is secured by encircling elasticized threads as indicated by 612, 614, 616, and 618.

In some embodiments, at the step illustrated by FIG. 6B, a dry coating of an indicator dye is sprayed onto the top of the cone as a biosensor or color guard. The indicator dye is chosen such that upon coming into contact with urine it will change color showing to the user that the male urinary incontinence device is now moist and should be changed. For example, the indicator dye could be red cabbage (anthrocyanin) mixed with sodium hydroxide to yield a neutral beige color in the absence of a non-alkaline liquid such as normal urine.

In another embodiment, a biosensor is implanted on the inside tip of the device. The biosensor can be a passive indicator of the presence of urine or an indicator of a disease state of the user, for example, via use of color changes, such as those of urine test strips, to be observed by self-examination, or, in the preferred embodiment, a real-time monitor of a disease state by an active RFID system as shown in FIG. 5 for sensing one or more conditions and transmitting the results using Near Field Communication (NFC), e.g., BlueTooth® to the user's FitBit® or iWatch® or other data collecting device. BlueTooth® is a registered trademark of Bluetooth Special Interest Group having an office at 5209 Lake Washington Blvd NE, Suite 350, Kirkland, Wash. 98033.

In FIG. 5 the battery, 506, can be an economical, low-powered, ultrathin zinc-carbon battery, a wafer-thin, lithium battery, or a bioelectric battery powered by the thermal gradient between the surface body temperature of the user in close contact with the inward facing portion of the sensor and the ambient temperature on the outfacing back of the sensor, which amounts to 2-deg C. or more. In the preferred embodiment, said bioelectric battery could be a conventional thermoelectric generator using the Seebek effect with a bimetallic junction, which is capable of using body heat to generate 200 millivolts, or a more compact, highly doped semiconductor using silicon-germanium, bismuth telluride, lead telluride or calcium manganese oxide, or one or more zinc oxide nanowires, or carbon nanotubes, which are capable of using body heat to generate an electric charge. The diagnostic circuitry, 504, is powered by the battery incorporating differential absorbance of chromogens used in the biosensor, 502, generating a status able to be interrogated by a nearby electronic device, such as an office laptop computer or smartphone, or able to be actively transmitted using Near Field Communication (NFC), for example, BlueTooth® to the user's FitBit® or iWatch® or other data collecting device. The diagnostic circuitry, 504, comprises an integrated antenna on an RFID chip adapted for information transmission that receives information from the biosensor, 502, a CMOS-compatible circuitry adapted to sense a chemical and/or physical quantity from a local environment in the male incontinence device using techniques described by Burke and Rutherglen (U.S. Pat. No. 8,830,037) and by Edmondson et al. (U.S. Pat. No. 7,229, 821) which are both herein incorporated by reference.

In FIG. 7 is shown an exemplary table of disease conditions diagnosable from urine in contact with the biosensor, 502. As with urinalysis which utilizes urine test strips that are briefly dipped in urine, excreted urine briefly contacts the sensing surface of the biosensor, 502, before the urine is wicked away by the superabsorbent layer of the male incontinence device. Within 1 or 2 minutes, the brief fluid exposure leads to differential chemical changes or an immobilized monolayer of antibodies which reacts with biological molecules in the urine depending on the structure chosen for the antibodies.

The biosensor, 502, can signal the onset time of urine release as well as the amount of urine released, which is a function of the duration of urine exposure from initial onset measured by said biosensor, 502, before the urine is absorbed by the superabsorbent material of the invention device. Tracking of onset time and the amount of urine released are useful metrics for tracking patient recovery from post-prostatectomy procedures. In addition, the effectiveness of pelvic floor exercise on the reduction in the occurrence of stress-related urinary incontinence may be tracked over time at a data integrative level, such as the user's smart watch or laptop.

The biosensor, 502, is able to detect a number of overall states and conditions of the excreted urine, such as the pH level, but also chemical and biological substances indicative of potential or actual diseases. As shown in the first row of the table of FIG. 7, the presence of protein in the urine would be detectable by means of a chromogen reaction. Such a condition, protouria, is frequently indicative of damage to the kidneys. As shown in the second row of the table of FIG. 7, the presence of hemoglobin (blood) in the urine would be detectable by means of a chromogen reaction. Such a condition, hematuria, is frequently indicative of kidney disease, such as kidney stones, glomerular disease, urinary tract infection or tumor. As shown in the third row of the table of FIG. 7, the presence of glucose in the urine would be detectable by means of a chromogen reaction whose intensity correlated with the amount of glucose. Such a condition, glucouria, is frequently indicative of a metabolic disease such as diabetes mellitus. As shown in the fourth row of the table of FIG. 7, the presence of ketone in the urine would be detectable by means of a chromogen reaction. Such a condition, ketouria, is frequently indicative of a metabolic imbalance such as diabetes type I. As shown in the fifth row of the table of FIG. 7, the presence of bilirubin in the urine would be detectable by means of a chromogen reaction. Such a condition, bilirubinuria, is frequently indicative of liver disease such as cirrhosis and the source of jaundice. As shown in the sixth row of the table of FIG. 7, the presence of leukocytes in the urine would be detectable by means of a chromogen reaction. Such a condition, leukocyturia, is frequently indicative of bacterial urinary infection. Similarly, nitrites could be detected, which are also indicative of nitrite-reducing bacteria, particularly gram negative bacteria. In both such cases, the biosensor tests would serve to indicate a need for more definitive diagnostics by, for example, urine analysis of a sample of the mid-stream flow of urine into a urine test receptacle. As shown in the seventh row of the table of FIG. 7, the presence of prostate specific antigen in the urine would be detectable by means of an immunoassay reaction. The presence of protein specific antigen is frequently indicative of prostate hyperplasia, prostatitis, or prostate tumor. A similar immunoassay would be able to detect PSMA3SA, which is more specific for a prostate adenocarcinoma. Similar immunoassays could detect circulating tumor cells, such as those from a bladder tumor.

While described with specific embodiments, it is understood that other variations of the invention are possible and are intended to be included. The scope of the invention is to be limited only by the scope of the claims.

The embodiments of the invention in which an exclusive property or privilege is claimed are defined as follows:

1. An apparatus for incontinent users, comprising: a cylindrical structure contoured to be fitted and placed around a phallus and meatus of the user without testicular restraint to maintain skin integrity thus avoiding skin abrasion with scrotum shear and contoured to provide discreet protection against socially embarrassing incontinence from light to moderate drips and dribbles by means of a small, light-weight incontinence protector; said apparatus further comprising: a dry coating of colorimetric indicator dye operable to change color when saturated with urine for conditions including: pH level in the user's urine, presence of protein in the user's urine, presence of blood in the user's urine, presence of glucose in the user's urine, presence of ketone in the user's urine, presence of bilirubin in the user's urine, presence of leukocytes in the user's urine, and presence of nitrites in the user's urine; said apparatus further comprising an active RFID biosensor implanted on inside tip of said apparatus to continuously read said colorimetric dye and operable to transmit, in real-time, information gathered by said biosensor via Near Field Communication; said biosensor to detect, by non-invasive immunoassays of the user's urine, health conditions including: presence of prostate specific antigen, presence of PSMA3SA, and presence of circulating tumor cells; said apparatus being compatible with men's apparel including boxers, close fitting trousers and jeans; and said apparatus having a design operable to be carried discretely by the user.

2. The apparatus of claim 1, further comprising hydrogel means for reliably wicking away urine when used by an active wearer without giving a wet or clammy feeling when in use and providing protection from odors while being easily positioned and applied and further comprising a battery for said biosensor taken from the group comprising low-powered, ultrathin zinc-carbon batteries, wafer-thin lithium batteries, and bioelectric batteries powered by thermal gradient between surface body temperature of the user and ambient temperature on outfacing back of said biosensor.

3. The apparatus of claim 1, wherein the cylindrical structure has a heat-sealed outer liquid-impermeable surface, a super absorbent hydrogel filling, and an inner liquid permeable layer spun-bonded to the super absorbent hydrogel filling, wherein a base of said cylindrical structure has one or more elasticized threads connected to a fastener and where said superabsorbent material is operable to retain urine odorlessly and wherein said elasticized threads are connected to said fastener by adhesive taken from the group comprising glue, cold-glue, hotmelt, lacquer, wax, reusable, re-sealable zippers, and hook-and-loop fasteners.

4. The apparatus of claim 3, further comprising a top portion of said super absorbent hydrogel filling serving as a color guard to alert the user with an externally marked color change when the apparatus is moist and needs to be replaced.

5. The apparatus of claim 1, further comprising adjustments of said apparatus operable to be actuated in a single step via a single-step releasable fastener.

6. The apparatus of claim 1, further comprising said apparatus being light-weight.

7. The apparatus of claim 1, further comprising said apparatus operable to monitor sensor data for transmission to a wearable device including a wireless-enabled wearable technology device or a smartwatch.

8. The apparatus of claim 1, further comprising said apparatus reliably wicking away urine and protecting against odors.

9. The apparatus of claim 1, wherein said biosensor is embedded in the top of an inner layer, said biosensor operable to detect components of the user's urine related to health conditions and to measure the excreted urine volume.

* * * * *